United States Patent
Jinwal et al.

(10) Patent No.: US 9,844,519 B1
(45) Date of Patent: Dec. 19, 2017

(54) METHOD OF TREATING TDP-43 PROTEINOPATHIES USING HEXACHLOROPHENE

(71) Applicants: Umesh K. Jinwal, Tampa, FL (US); Diego A. Peralta, Pembroke Pines, FL (US); Malathi Narayan, Tampa, FL (US)

(72) Inventors: Umesh K. Jinwal, Tampa, FL (US); Diego A. Peralta, Pembroke Pines, FL (US); Malathi Narayan, Tampa, FL (US)

(73) Assignee: University of South Florida, Tampa, FL (US)

(*) Notice: Subject to any disclaimer, the term of this patent is extended or adjusted under 35 U.S.C. 154(b) by 145 days.

(21) Appl. No.: 14/742,164

(22) Filed: Jun. 17, 2015

Related U.S. Application Data (60) Provisional application No. 62/013,260, filed on Jun. 17, 2014.

(51) Int. Cl.
    *A61K 31/055* (2006.01)
    *A61K 45/06* (2006.01)

(52) U.S. Cl.
    CPC ............ *A61K 31/055* (2013.01); *A61K 45/06* (2013.01)

(58) Field of Classification Search
    CPC .................................................. A61K 31/055
    See application file for complete search history.

(56) References Cited

U.S. PATENT DOCUMENTS

2013/0116215 A1* 5/2013 Coma .................. A61K 31/165
    514/108

OTHER PUBLICATIONS

Fang, YS et al., Full length TDP-43 forms toxic amyloid oligomers that are present in the frontotemporal lobar lementia-TDP patients, Nature Communications, (2014), 5:4824, pp. 1-13.

Guo, W. et al., An ALS-associated mutation affecting TDP-43 enhances protein aggregation, fibril formation and neurotoxicity, Nature Structural & Molecular Biology, 2011, vol. 18, No. 7, pp. 822-830.

McKee, A. et al., TDP-43 proteinopathy and motor neuron disease in chronic traumatic encephalopathy, J Neuropathol Exp Neurol., 2010, vol. 69, No. 9, pp. 918-929.

Hanig, J.P. et al., Protection with butylated hydroxytoluene and other compounds against intoxication and mortality caused by hexachlorophene, Fd Chem. Toxic, 1984, vol. 22, No. 3, pp. 185-189.

Yapar, K. et al., Protective effects of L-carnitine on the hexachlorophene-induced neurotoxicity and oxidative stress in mice, Revuede Medecine Veterinaire, 2007, vol. 158, No. 12, pp. 607-612.

(Continued)

*Primary Examiner* — Benjamin Packard
(74) *Attorney, Agent, or Firm* — Michele L. Lawson; Smith & Hopen, P.A.

(57) ABSTRACT

A method of treating TDP-43 proteinopathies such as Alzheimer's disease, amyotrophic lateral sclerosis, and fronto-temporal lobar dementia is presented herein. It was found that administering hexachlorophene to cells expressing endogenous TDP-43 or overexpressing wild-type TDP-43 reduced accumulation of TDP-43 in the cells.

12 Claims, 9 Drawing Sheets

(A) ICW optimization (B) Drug Screening (C) Quantification (56) References Cited

OTHER PUBLICATIONS

Eleuteri S. et al., Novel therapeutic strategy for neurodegeneration by blocking Aβ seeding mediated aggregation in models of Alzheimer's disease, Neurobiology of Disease, 2015, 74, pp. 144-157.

Zhang, T. et al., TDP-43 neurotoxicity and protein aggregation modulated by heat shock factor and insulin/IGF-1 signaling, Human Molecular Genetics, 2011, vol. 20, No. 10, pp. 1952-1965.

* cited by examiner (A) ICW optimization (B) Drug Screening (C) Quantification

METHOD OF TREATING TDP-43 PROTEINOPATHIES USING HEXACHLOROPHENE

CROSS REFERENCE TO RELATED APPLICATIONS

This application is a nonprovisional of and claims priority to U.S. Provisional Patent Application No. 62/013,260, entitled "Method of Treating TDP-43 Proteinopathies Using Hexachlorophene", filed Jun. 17, 2014, the entire contents of which is herein incorporated into this disclosure.

FIELD OF INVENTION

This invention relates to treating neurodegenerative diseases. Specifically, the invention describes methods of treating TDP-43 proteinopathies such as Alzheimer's disease (AD), amyotrophic lateral sclerosis (ALS), and fronto-temporal lobar dementia (FTLD) using hexachlorophene.

BACKGROUND OF THE INVENTION

TDP-43 (TAR DNA binding protein of 43 kDa) is a 414 amino acid DNA- and RNA-binding protein that was identified based on its binding to the HIV-1 TAR DNA sequence. While its function is not fully understood, TDP-43 is implicated in transcriptional repression, exon splicing, miRNA generation, cell cycle regulation and apoptosis. The protein contains two RNA recognition motifs (RRM1 and 2) and a C-terminal glycine-rich domain. Ubiquitinated, phosphorylated and insoluble forms of TDP-43 are identified as constituents of inclusions found in TDP-43 proteinopathies that include amyotrophic lateral sclerosis (ALS) and frontotemporal lobar dementia (FTLD) and Alzheimer's disease (AD) (Arai et al., 2006; Josephs et al., 2014; Neumann et al., 2006).

Wildtype (WT) TDP-43 contains two nuclear localization signals (NLS) in the N-terminal domain of the protein and predominantly localizes to the nucleus; however, truncation mutants lacking the NLS sequences localize to the cytoplasm (Ayala et al., 2008; Winton et al., 2008). Proteolytic fragments (e.g. C25) and higher molecular weight species of TDP-43, including soluble oligomers and insoluble aggregates, localize to the cytoplasm and are associated with toxicity. The accumulation of TDP-43 leads to a loss of cellular function, thereby impairing the viability of the affected nerve cells. Disease associated point mutations in TDP-43, of which 32 have been identified, are primarily located in the C-terminal domain (Pesiridis et al., 2009). While the role of these mutations in causing disease is not fully understood, pathological forms of TDP-43 identified in AD, ALS and FTLD include higher molecular weight, aggregated TDP-43, which is often phosphorylated and ubiquitinated.

In the AD brain TDP-43 pathology can present as cytoplasmic and intranuclear inclusions in neurons. TDP-43 pathology in AD is associated with an increased risk for hippocampal atrophy, memory loss and cognitive impairment. Recent data from another group suggests that TDP-43 plays a key role in AD pathogenesis and that people with TDP-43 pathology were at a greater risk for hippocampal atrophy, memory loss and cognitive impairment.

It has recently been suggested that TDP-43 oligomers, aside from filamentous aggregates, may play a role in TDP-43 pathogenesis. It was found that recombinant full-length human TDP-43 forms structurally stable, spherical oligomers that share common epitopes with an anti-amyloid oligomer-specific antibody. The TDP-43 oligomers are stable, have exposed hydrophobic surfaces, exhibit reduced DNA binding capability and are neurotoxic in vitro and in vivo. Moreover, TDP-43 oligomers are capable of cross-seeding Alzheimer's amyloid-beta to form amyloid oligomers, demonstrating interconvertibility between the amyloid species. Such oligomers are present in the forebrain of transgenic TDP-43 mice and FTLD-TDP patients. (Fang, Y S et al., Full length TDP-43 forms toxic amyloid oligomers that are present in the frontotemporal lobar dementia-TDP patients, *Nature Communications*, (2014), 5:4824)

There is some evidence that the C-terminus of TDP-43 shows sequence similarity to prion proteins which raises the possibility that TDP-43 derivatives may cause spreading of the disease phenotype among neighboring neurons. Synthetic peptides flanking residue 315 form amyloid fibrils in vitro and cause neuronal death in primary cultures. Given the biochemical similarities between TDP-43 and prion proteins, there may be therapeutic potential for decreasing the abundance of neurotoxic TDP-43 species, enhancing degradation or clearance of such TDP-43 derivatives and blocking the spread of the disease phenotype. (Guo, W. et al., An ALS-associated mutation affecting TDP-43 enhances protein aggregation, fibril formation and neurotoxicity, *Nature Structural & Molecular Biology*, 2011, 18:822-830)

ALS is a fatal progressive degeneration of motor neurons in the brain and spinal cord. Whereas 90% to 95% of ALS cases are sporadic, gene mutations in copper/zinc superoxide dismutase 1, senataxin, dynactin, angiogenic, and TAR-DBP (the gene for transactive response DNA-binding protein of 43 kd [TDP-43] on chromosome 1) account for some familial forms of the disease. Although TDP-43 was originally thought to be a specific marker for ALS and frontotemporal lobar degeneration (FTLD) with tau-negative ubiquitin-positive TDP-43-positive inclusions (FTLD-U, recently renamed FTLD-TDP), TDP-43-positive inclusions have now been found in a variety of other neurodegenerative disorders. Diseases with secondary TDP-43 pathology include AD and hippocampal sclerosis, Guam parkinsonism-dementia complex (PDC), Pick disease, corticobasal degeneration, argyrophilic grain disease, and Lewy body disease. (McKee, A. et al., TDP-43 proteinopathy and motor neuron disease in chronic traumatic encephalopathy, *J Neuropathol Exp Neurol.*, 2010, 69(9):918-929)

It has been suggested that repetitive head injury is associated with the development of chronic traumatic encephalopathy (CTE). Patients suffering from CTE have recently been shown to have TDP-43 proteinopathy affecting the frontal and temporal cortices, medial temporal lobe, basal ganglia, diencephalon and brainstem. The TDP-43 proteinopathy associated with CTE is similar to that found in frontotemporal lobar degeneration with TDP-43 inclusions, in that widespread regions of the brain are affected. Akin to frontotemporal lobar degeneration with TDP-43 inclusions, in some individuals with CTE, the TDP-43 proteinopathy extends to involve the spinal cord and is associated with motor neuron disease. It is thought that traumatic axonal injury may also accelerate TDP-43 accumulation, aggregation, and dislocation to the cytoplasm and thereby enhance its neurotoxicity. (McKee 2010)

Hexachlorophene (also referred to herein as B10), an organochlorine compound, was widely used as an effective antiseptic for topical applications until the 1970s (Kimbrough, 1971; Pilapil, 1966). It has been found to cause toxicity in animal models (Kimbrough and Gaines, 1971; Thorpe, 1967), and its use was discontinued due to the severity of side effects in human beings. It is generally prepared by the condensation of 2 moles of 2,4,5-trichlorophenol with 1 mole formaldehyde in the presence of concentrated sulfuric acid. B10 can be absorbed into the body through the skin or by ingestion. Oral toxicity studies in rats show an LD50=66 mg/kg.

It has been shown to inhibit the Wnt-β-catenin signaling pathway in B lymphoma cells (Min et al., 2009), and recently to inhibit amyloid beta (Aβ) fibril formation and protect primary neuronal cultures from Aβ-induced toxicity (Eleuteri et al., 2014).

In overcoming the toxicity of hexachlorophene (B10) administration alone, another group found that pre-treatment with antioxidants, such as butylated hydroxytoluene (BHT) and ethoxyquin, prior to administration of B10 protects rats from toxicity induced by B10. BHT and ethoxyquin are both free-radical scavengers that prevent lipid peroxidation. In addition, this group also found that agents, such as phenobarbital and SKF-525A (2-diethylaminoethyl-2,2-diphenylvalerate-Hcl), also lessened toxicity when administered prior to B10. The pre-treatment agents were administered daily for at least 3 days prior to administration of B10. It was noteworthy that the protective effect of SKF-525A only occurred upon oral administration of the drug, not ip administration. It was suggested that this effect may occur because a higher SKF-525A is a cytochrome P450 inhibitor which is known to potentiate barbiturate effects and phenobarbital is a barbiturate itself (Hanig, J. P. et al., Protection with butylated hydroxytoluene and other compounds against intoxication and mortality caused by hexachlorophene, *Fd Chem. Toxic.*, 22(3):185-189)

A different group also noted that pre-treatment with the antioxidant L-carnitine also protected rats from the toxicity of B10. (Yapar, K. et al., Protective effects of L-carnitine on the hexachlorophene-induced neurotoxicity and oxidative stress in mice, *Revuede Medecine Veterinaire*, 2007, 158 (12):607-612)

Given the limited options that exist for treatment of TDP-43 proteinopathies, what is needed is a drug that is capable of reducing TDP-43 expression in patients suffering from TDP-43 proteinopathies. It would be advantageous to identify pharmacological agents that may inhibit the formation of TDP-43 aggregates or aid in the clearance of such aggregates from cells.

SUMMARY OF INVENTION

Briefly, using a novel InCell Western (ICW) method, over 300 drugs were screened that target TDP-43. It was found that B10 effectively reduces levels of TDP-43 and its mutants in cell culture models. Validation experiments using B10 showed reduction of both endogenous TDP-43 in N9 microglial cells and over-expressed TDP-43 in HEK293 and HeLa cells. The effect of B10 on various pathological forms of TDP-43 such as the C25 cleaved fragment that localizes to the cytosol, insoluble high molecular weight species, and ALS-linked mutants (Q331K and M337V) was also analyzed. It was found that B10 clears all pathological forms of TDP-43 including insoluble, higher molecular weight species. These data indicate that B10 may be a viable drug candidate for modulation of levels of pathological TDP-43 in the treatment of ALS and other TDP-43 proteinopathies.

A method of treating a neurodegenerative disease characterized by accumulation of TDP-43 protein in a patient in need thereof is presented comprising administering a therapeutically effective amount of a TDP-43 targeting drug. The neurodegenerative disease can be amyotrophic lateral sclerosis (ALS), Alzheimer's disease (AD) or fronto-temporal lobar dementia (FTLD) and the TDP-43 targeting drug can be hexachlorophene.

In some embodiments, the TDP-43 targeting drug may be encapsulated in a vesicle prior to administration to the patient where the vesicle is selected from the group consisting of liposomes, niosomes, micelles, multilamellar vesicles, unilamellar vesicles, and polymersomes.

In other embodiments, a pre-administration agent may be administered at a time period prior to administration of the TDP-targeting drug. The pre-administration agent may be an antioxidant selected from the group consisting of butylated hydroxytoluene (BHT), ethoxyquin and L-carnitine. Additional pre-administration agents include phenobarbital and SKF-525A. In some embodiments, the pre-administration agent may be administered to the patient at least once per day for at least one day prior to administration of the TDP-targeting drug.

A method of decreasing TDP-43 accumulation in cells is presented comprising contacting the cells with a therapeutically effective amount of hexachlorophene or a derivative thereof. In some embodiments, the cells may be contacted with a pre-administration agent at a time period prior to administration of the hexachlorophene or derivative thereof. The pre-administration agent may be selected from the group consisting of butylated hydroxytoluene (BHT), ethoxyquin, L-carnitine, phenobarbital and SKF-525A. In other embodiments, the hexachlorophene or derivative thereof may be encapsulated in a vesicle prior to contacting the cells. The vesicle may be selected from the group consisting of liposomes, niosomes, micelles, multilamellar vesicles, unilamellar vesicles, and polymersomes.

A method of inhibiting formation of TDP-43 aggregates in cells is presented comprising contacting the cells with a therapeutically effective amount of hexachlorophene or a derivative thereof. In some embodiments, the cells may be contacted with a pre-administration agent at a time period prior to administration of the hexachlorophene or derivative thereof. The pre-administration agent may be selected from the group consisting of butylated hydroxytoluene (BHT), ethoxyquin, L-carnitine, phenobarbital and SKF-525A. In other embodiments, the hexachlorophene or derivative thereof may be encapsulated in a vesicle prior to contacting the cells. The vesicle may be selected from the group consisting of liposomes, niosomes, micelles, multilamellar vesicles, unilamellar vesicles, and polymersomes.

BRIEF DESCRIPTION OF THE DRAWINGS

For a fuller understanding of the invention, reference should be made to the following detailed description, taken in connection with the accompanying drawings, in which:

FIG. 1A-C is a series of images depicting the optimization of ICW and identification of candidate drug molecules that decrease TDP-43 levels. (A) N9 cells were fixed and processed for ICW with the TDP-43 and GAPDH antibodies, which used at a dilution of 1:1000 and 1:3000, respectively. Primary antibody only and secondary antibody only were included as controls. Fluorescence intensity was recorded and quantified using the Odyssey Infrared Imaging System (LI-COR). (B) N9 cells were treated with various drugs for 24 hours and processed for ICW assay. (C) Quantification of fluorescence intensity showed that B10 had the greatest effect on TDP-43 compared to other drugs. Averages and SEM are representative of two experiments (n=2).

FIG. 2A-D is a series of images depicting B10 decreases levels of TDP-43 and its mutants. (A) N9 cells expressing endogenous TDP-43 were treated with various concentrations of B10 or DMSO control vehicle for 24 hours and analyzed by western blotting. (B) Quantification of Western blot showed B10 at 3 µM reduces endogenous TDP-43 levels ~50%. (C) Disease-associated mutant forms of TDP-43 were transfected in HEK 293 cells and treated with 3 µM B10 for 24 hours. (D) Quantification of western blot showed B10 approximately 50% decrease in levels of TDP-43 and its mutants. Averages and SEM are representative of two experiments (n=2).

FIG. 4A-B is a series of images depicting B10 reduces levels of insoluble higher molecular weight species of TDP-43. HEK293 cells were transfected with Myc-tagged TDP-43 and treated with 3 µM B10 with and without MG132 for 24 hours. Samples were separated using centrifugation into soluble and insoluble fractions. (A) Western blot analysis showed that B10 reduces levels of non-aggregated soluble TDP-43. (B) Western blot analysis with insoluble fraction showed that B10 reduces levels of insoluble TDP-43 and higher molecular weight (HMW) species. Insoluble TDP-43 is shown at darker and lighter exposures, respectively. The figure is representative of two experiments (n=2).

FIG. 5A-B is a series of images depicting B10 does not induce excessive cytotoxicity. (A) N9 cells were treated with 3 and 10 µM B10 for 24 hours and cytotoxicity was assessed by determining LDH release. B10 causes ~6% and ~23% cytotoxicity at 3 and 10 µM in the N9 cells, respectively. (B) HEK293 cells were treated with 3 and 10 µM B10 for 24 hours and cytotoxicity was assessed by determining LDH release. B10 causes ~3% and ~13% cytotoxicity at 3 and 10 µM in the HEK293 cells, respectively. Averages and SEM are representative of three experiments (n=3).

FIG. 6A-C is a series of images depicting B10 reduces levels of TDP-43, but increases levels of FUS. (A) HEK293 cells expressing endogenous TDP-43 and FUS were treated with 3, 10 µM B10, and DMSO vehicle control for 24 hours and analyzed by Western blotting. (B and C) Quantification of Western blot showed B10 at 3 µM increases FUS levels by ~300%, but reduces TDP-43 levels ~50%. Averages and SEM are representative of three experiments (n=3).

FIG. 9A-B are a series of images depicting B10 decreases cytoplasmic aggregates of C25-TDP-43 in a transgenic *C. elegans* model. A) Neurons in the head region of C25-TDP-43 expression transgenic *C. elegans* are shown; B) Graph depicting the area of fluorescence for neurons treated with DMSO versus B10.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the compositions or any combination thereof is that amount necessary to provide a therapeutically effective result in vivo or in vitro, including, but not limited to, total prevention of (e.g., protection against) and to improved survival rate or more rapid recovery, or improvement or elimination of symptoms associated with neurodegenerative disorders, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The term "vesicle" or "nanoparticle vesicle" as used herein refers to small bubble-like vesicles that may be used as a drug-delivery system. The vesicles may be comprised of lipids such as phospholipids, cholesterol and non-ionic surfactants, copolymers, biodegradable and biocompatible polymers such as chitosin, PLA, PLGA, and starch. Drugs may be encapsulated within the nanoparticle vesicle to enhance bioavailability of the drug. Nanoparticle vesicles include, but are not limited to, liposomes, niosomes, micelles, multilamellar vesicles, unilamellar vesicles, and polymersomes. The nanoparticle vesicles can be between 1 nm and 250 nm (generally over 100 nm) and can encapsulate the drug to be delivered. In some embodiments, these may vesicles self-assemble during preparation. While the nanoparticle vesicles can range in size, in some embodiments the nanoparticle vesicles may be between 30 nm and 80 nm so as to be able to pass the blood-brain barrier.

"Pre-treatment agent" or "pre-administration agent" as used herein refers to a first agent that is administered, in vitro or in vivo, at a time period prior to the administration of a second agent. In some embodiments, the first agent is an a composition that reduces at least one adverse effect of the second agent, including reducing toxicity of the second agent or enhancing the treatment effect of the second agent, in some instances this enhancement may be in an additive or synergistic manner. In some embodiments, the first agent is an agent which reduces the toxicity of hexachlorophene (the second agent) including, but not limited to, butylated hydroxytoluene (BHT), ethoxyquin, L-carnitine, phenobarbital, and SKF-525A.

"Administration" or "administering" is used to describe the process by which the compounds of the present invention, or any combination thereof, are delivered to a patient. The composition may be administered in various ways including parenteral (referring to intravenous and intraarterial and other appropriate parenteral routes), intratheceal, intraventricular, intracisternal, intranigral, oral, transdermally, subcutaneously, and other routes that allow the composition to contact neurons. The compositions of the invention may be administered independently or in combination with other compounds. Administration will often depend on the disease and level of progression in the afflicted brain.

"Active agent" as used herein is defined as a substance, component or agent that has measurable specified or selective physiological activity when administered to an individual in a therapeutically effective amount. Examples of active agents as used in the present invention include TDP-43 targeting drugs such as hexachlorophene and its derivatives. At least one active agent is used in the compositions of the present invention.

The terms "pharmaceutical compositions", "drugs", "agents" and "compounds" are used interchangeably herein to refer to a molecule, a group of molecules, a complex or substance containing an active agent that is administered to a subject for diagnostic, therapeutic, preventative, medical, or veterinary purposes. Included are externally and internally administered topical, localized and systemic human and animal pharmaceuticals, treatments, remedies, nutraceuticals, biologicals, and diagnostics, including preparations useful in clinical and veterinary screening, prevention, prophylaxis, healing, wellness, detection, imaging, diagnosis, therapy, surgery, monitoring, and the like.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. To prepare the pharmaceutical compositions of this invention, the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, vaginally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. Eleuteri et al. found 50% brain permeability of hexachlorophene at a dose of about 10 mg/kg for a transgenic TDP43 mouse model. (Eleuteri S. et al., Novel therapeutic strategy for neurodegeneration by blocking Aβ seeding mediated aggregation in models of Alzheimer's disease, *Neurobiology of Disease*, 2015, 74:144-157). Based on these results, an exemplary in vivo dosage is about 10 mg/kg. This dose can be adjusted downward to establish a minimum dosage in vivo and can be adjusted upwards to establish a maximum dosage in vivo for the present invention as is known by those of skill in the art.

The compounds used in the present invention may be administered individually, or in combination with or concurrently/concomitantly with one or more other compounds used in other embodiments of the present invention.

The term "neurodegenerative disease" is used throughout the specification to identify a disease which is caused by damage to the central nervous system and can be identified by neuronal death. Further, the term "neurodegenerative disease" as used herein describes "neurodegenerative diseases" which are associated with increased levels of TDP-43 or aggregates of TDP-43. Exemplary neurodegenerative diseases include, but are not limited to, TDP-43 proteinopathies such as hippocampal sclerosis, Guam parkinsonism-dementia complex (PDC), Pick disease, corticobasal degeneration, argyrophilic grain disease, Lewy body disease, Huntington's disease, Down Syndrome, Hippocampal sclerosis dementia, Familial British dementia, Spinal Cerebellar ataxia Alzheimer's disease (AD), amyotrophic lateral sclerosis (ALS), and fronto-temporal lobar dementia (FTLD).

"TDP-43 proteinopathies" as used herein refers to a group of diseases associated with ubiquitinated, phosphorylated and insoluble forms of TDP-43 accumulating in the brain. These diseases include, but are not limited to, amyotrophic lateral sclerosis (ALS), fronto-temporal lobar dementia (FTLD), Alzheimer's disease (AD), chronic traumatic encephalopathy (CTE), hippocampal sclerosis, Guam parkinsonism-dementia complex (PDC), Pick disease, corticobasal degeneration, argyrophilic grain disease, Lewy body disease, Huntington's disease, Down Syndrome, Hippocampal sclerosis dementia, Familial British dementia, Spinal Cerebellar ataxia.

The term "amyotrophic lateral sclerosis" or "ALS" as used herein refers to a fatal degenerative disease affecting motor neurons in the spinal cord, brainstem, and cortex which clinically manifests as progressive muscular weakness and atrophy eventually leading to paralysis and death usually within 3-5 years of diagnosis.

The term "fronto-temporal lobar dementia" or "(FTLD)" as used herein refers to a progressive neurodegenerative disorder which is the second most common form of early-onset neurodegenerative dementia after AD. It affects between 10-20% of patients with an onset of dementia before age 65. FTLD patients present with prominent behavioral and personality changes as well as language impairment which eventually evolves into cognitive impairment and dementia. The most common neuropathology associated with clinical FLTD is frontal and anterior temporal lobe atrophy with neuronal inclusions immunoreactive for ubiquitin and TAR-DNA binding protein 43 (TDP-43), but negative for tau and α-synuclein (FTLD-U).

The term "Alzheimer's disease" or "AD" as used herein refers to a condition characterized by the abnormal deposition of amyloid in the brain of a patient in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the amyloid protein (Aβ) which is a proteolytic product of a precursor protein of much larger size. The symptoms of Alzheimer's disease are similar to those of other dementias and include, but are not limited to, memory loss, changes in personality, problems using language, disorientation, difficulty doing daily activities, and disruptive behavior. As described herein, "Alzheimer's disease" refers to both sporadic and familial (genetic) forms of the disease.

The term "TDP-43 targeting drugs" as used herein refers to pharmaceutical compositions such as small molecule inhibitors that inhibit TDP-43 expression or reduce TDP-43 levels or reduce TDP-43 aggregates in cells. An example of such a drug is hexachlorophene and its derivatives.

Optimization of ICW and Identification of Candidate Drug Molecules that Decrease TDP-43 Levels.

Figure 1A:
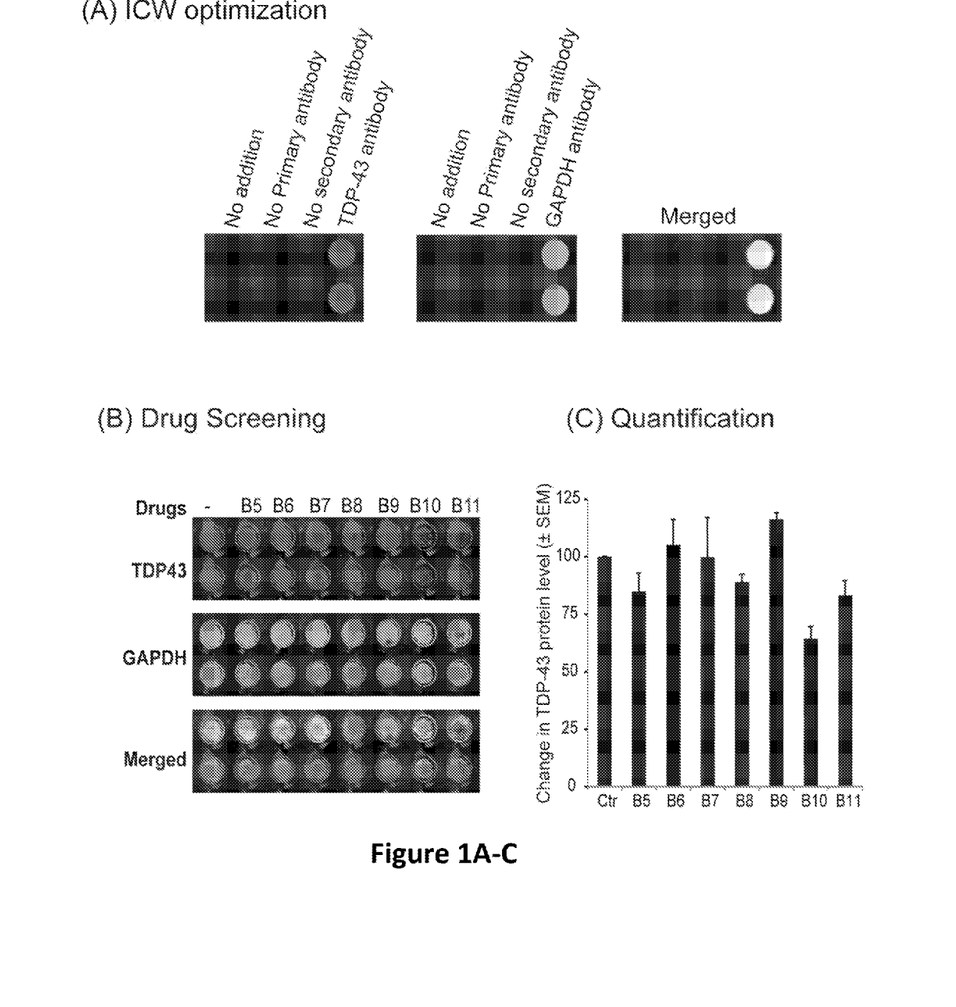

To optimize the ICW technique for screening TDP-43 targeting drugs, N9 cells were seeded in a 96-well plate and processed for ICW by using various dilution of TDP-43 antibody. TDP-43 antibody, used at a dilution of 1:1000, provided sufficient signal for detection (FIG. 1A).

For drug screening, N9 cells were treated with a panel of candidate drug molecules for 24 hours and the effect on TDP-43 levels was analyzed using the InCell Western assay. Of the drugs tested, the inventors found that hexachlorophene (also referred to herein as B10) had the greatest effect compared to the control causing ~40% decrease in levels of TDP-43 (FIGS. 1B and C). Based on its effect on TDP-43 levels, B10 was chosen was further analysis. The drugs used for the InCell Western analysis and the level of TDP-43 after treatment are shown in Table 1.

TABLE 1

Drugs for InCell Western Analysis and Level of TDP-43 After Treatment

| Treatment | Drug names | % TDP43 level |
|---|---|---|
| Ctr | DMSO-Vehicle control | 100 |
| B5 | Perphenazine | 85 |
| B6 | Rifampicin | 103 |
| B7 | Dapsone | 100 |
| B8 | Hydroflumethiazide | 89 |
| B9 | Dicyclomine | 115 |
| B10 | Hexachlorophene | 63 |
| B11 | Methyldopa | 81 |

B10 Decreases Levels of TDP-43 and its Mutants.

Figure 2A:
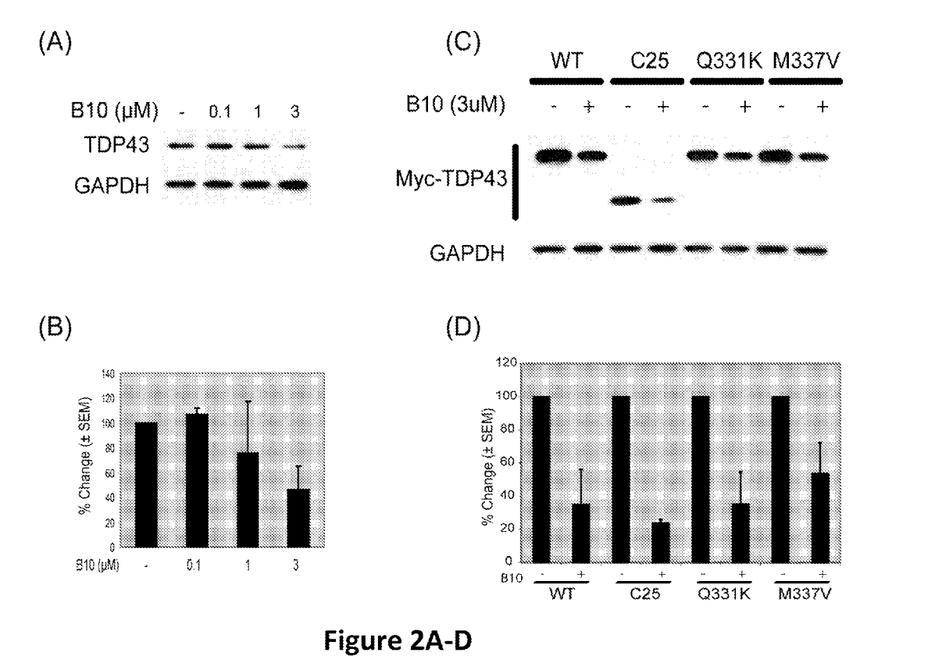

N9 cells were treated with different concentration of B10 for 24 hours and levels of endogenous TDP-43 were determined by Western blotting. B10 had the greatest effect on levels of TDP-43 at 3 µM, which decreased TDP-43 levels by ~50% (FIGS. 2A and B). To determine if B10 also decreases levels of mutant forms of TDP-43, HEK 293 cells were transfected with Myc-tagged WT TDP-43, the C25 mutant, and the point mutants M337V and Q331K, and treated with 3 µM B10 for 24 hours. Western blotting analysis showed that B10 decreases levels of TDP-43 and its mutants by approximately 50% (FIGS. 2C and D).

Figure 5A:
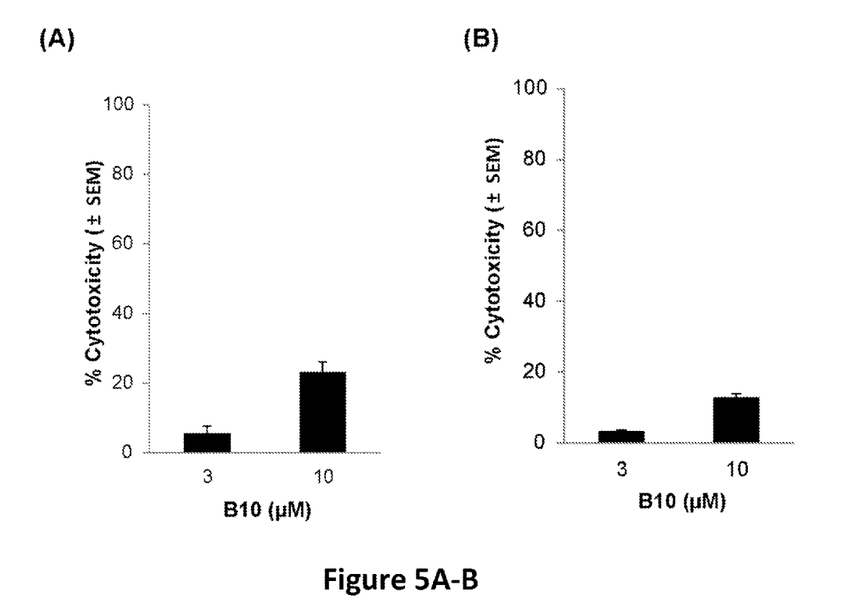

Whether B10 treatment causes cytotoxicity was next tested. The inventors performed the LDH assay with N9 and HEK293 cells. The inventors found that B10 treatment causes ~6% and ~23% cytotoxicity at 3 and 10 µM in the N9 cells, respectively (FIG. 5A). B10 causes ~3% and ~13% cytotoxicity at 3 and 10 µM in the HEK293 cells, respectively (FIG. 5B). Overall these data suggest that B10 does not induce excessive cytotoxicity.

Figure 6A:
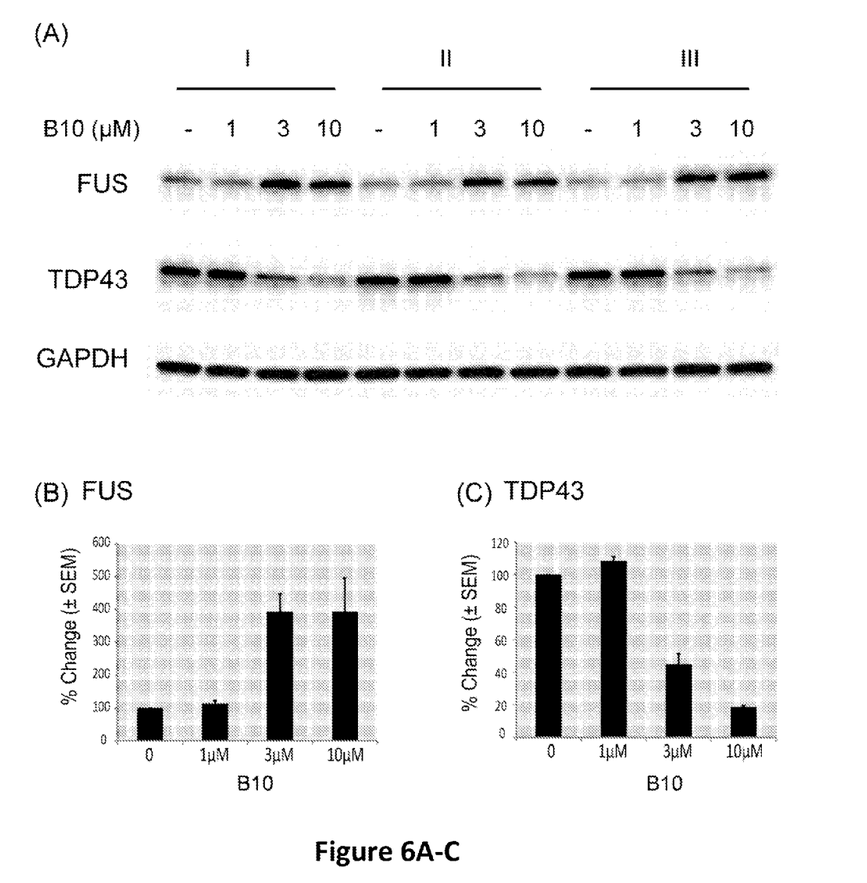

In order to determine whether B10 has similar effect on other ALS-linked proteins, the inventors tested FUS (Fused in Sarcoma), an RNA-binding protein whose mutants are also implicated in ALS (Kwiatkowski et al., 2009; Vance et al., 2009). Interestingly, treatment with B10 increases levels of FUS in HEK293 cells (FIG. 6), indicating that the reducing effect of B10 is specific to TDP-43. Overall, these data suggest that further investigation will elucidate the mechanism of action of B10 in modulating levels of other ALS-related proteins and pathways.

B10 Reduces Cytoplasmic TDP-43 Mutant C25.

Figure 3:
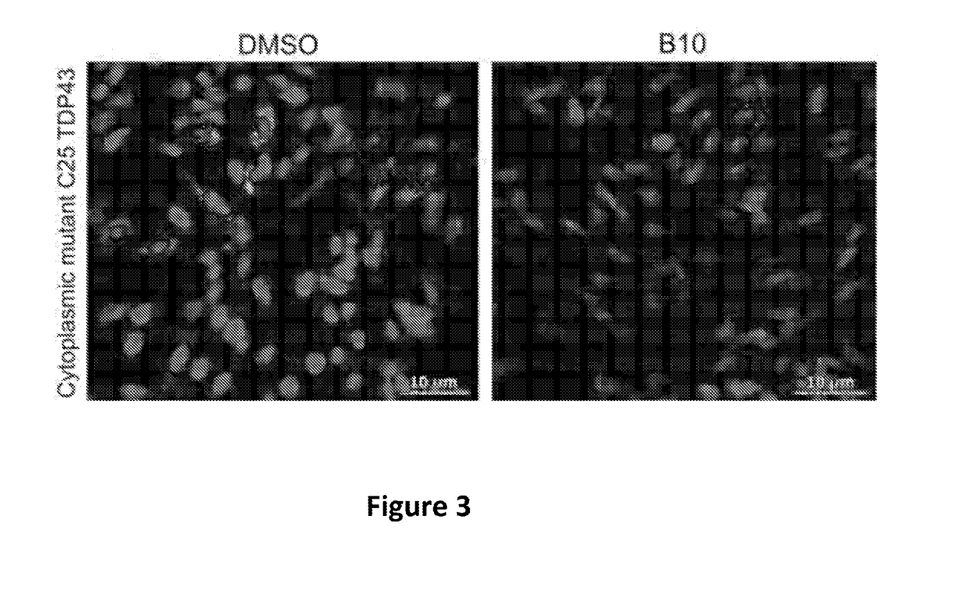
FIG. 3 is an image depicting B10 reduces cytoplasmic TDP-43 mutant C25. The Myc-tagged C25 mutant of TDP-43 lacks the NLS was transfected in HEK293 cells and treated with 3 µM B10 for 24 hours. Cells were fixed and incubated with a primary antibody to Myc and an Alexa488-tagged secondary antibody. Image analysis showed B10 treatment reduces the number of cells expressing cytoplasmic C25 mutant TDP-43. The images are representative of two experiments; scale bar represents 10 µm.

The C25 mutant of TDP-43 lacks the NLS and is localized predominantly to the cytoplasm of the cell, where it is prone to aggregation. To determine whether B10 decreases the number of cells with aggregates, immunofluorescence analysis was performed. HEK293 cells expressing the C25 mutant of TDP-43 were treated with either DMSO or 3 µM B10 and analyzed by immunofluorescence. It was found that B10 treatment decreases the amount of cytoplasmic C25 mutant TDP-43 in transfected cells (FIG. 3).

B10 Decreases Levels of Insoluble Higher Molecular Weight Species of TDP-43.

In addition to the point and truncation mutants of TDP-43, pathological forms include species that form insoluble, higher molecular weight (HMW) aggregates. To determine whether B10 decreases levels of HMW aggregates, HEK293 cells were transfected with Myc-tagged TDP-43 and separated into soluble and insoluble fractions. Levels of TDP-43 in each fraction were determined by Western blotting. Treatment with MG132 was used as a control, since it has been shown that inhibition of the proteasome increases accumulation of insoluble HMW TDP-43 and ubiquitinated proteins (van Eersel et al., 2011).

Figure 4A:
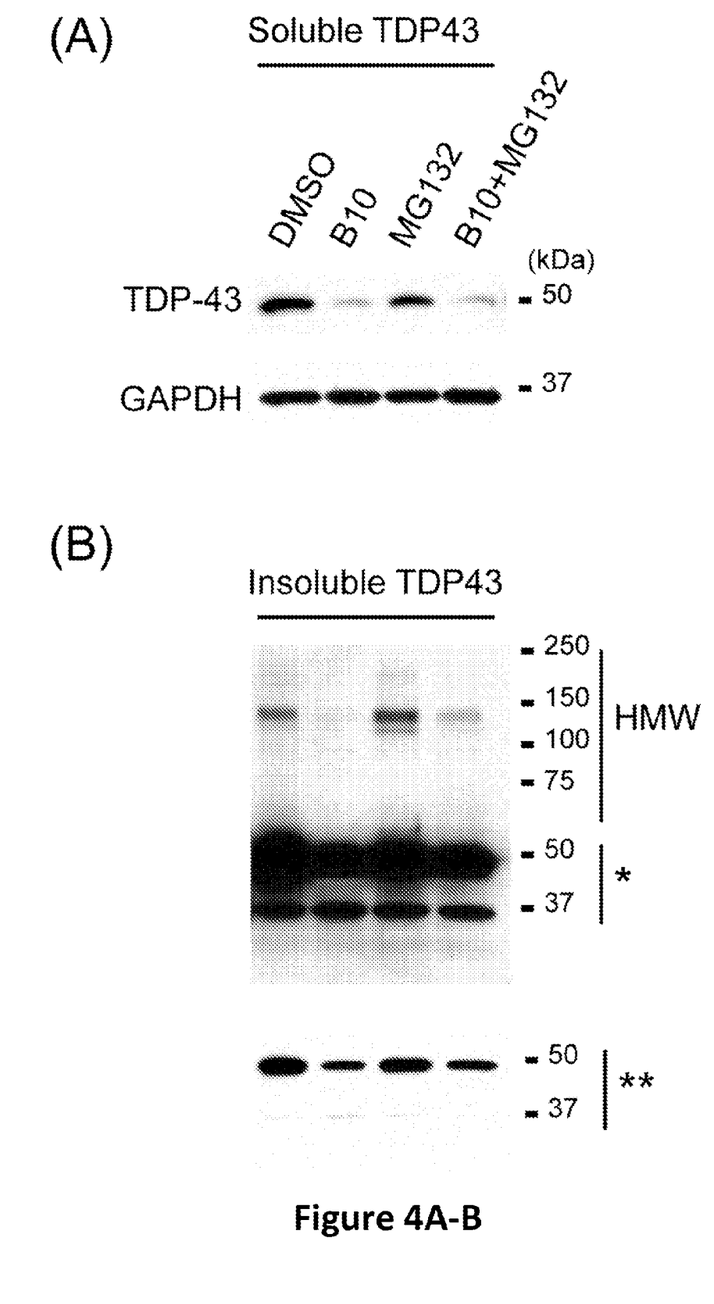
Figure 7:
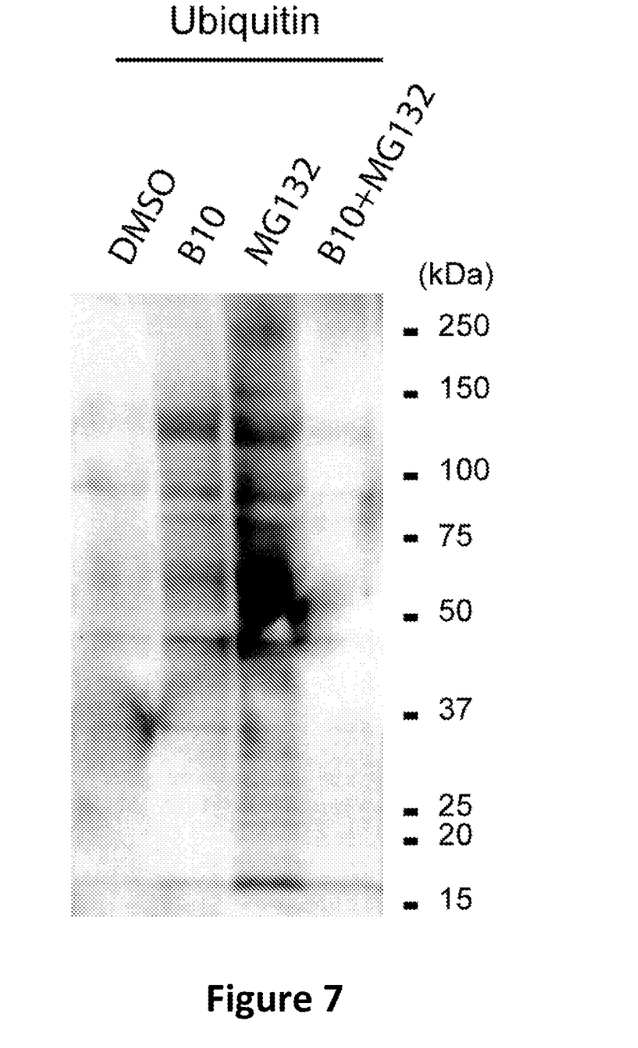
FIG. 7 is an image depicting MG132 treatment increases levels of ubiquitinated proteins. Samples from FIG. 4A were tested for the effect of MG132 on inhibition of proteasome. Western blot analysis showed that MG132 led to increase in ubiquitinated proteins. B10 treatment also showed slight increase in ubiquitinated proteins. Co-treatment with B10 and MG132 showed reduction in ubiquitinated proteins.

The inventors found that not only does B10 decrease levels of non-aggregated soluble (FIG. 4A) and insoluble TDP-43, but it also decreases HMW species in the insoluble fraction (FIG. 4B). Effect of MG132 on proteasome inhibition was confirmed by using ubiquitin antibody. Western blot analysis showed that MG132 led to increase in ubiquitinated proteins as expected (FIG. 7).

In Vivo Studies

For in vivo studies the inventors used a C. elegans model expressing the C25 fragment to analyze changes in behavior and pathological TDP-43 upon B10 treatment. The transgenic C. elegans model that expresses TDP-43 is described in detail in Zhang et al. 2011, herein incorporated by reference. (Zhang, T. et al., TDP-43 neurotoxicity and protein aggregation modulated by heat shock factor and insulin/IGF-1 signaling, Human Molecular Genetics, 2011, 20(10): 1952-1965).

The Solid Method of drug dosing was used in which age-synchronized C. elegans eggs were plated on Nematode Growth Media (NGM) plates containing DMSO vehicle or 5 µM B10 or 10 µM B10.

A behavioral assay that measures liquid thrashing ability was used to analyze the effect of B10 treatment on motility in age synchronized C25 animals. For microscopic analysis adult worms were fixed on slide and imaged using fluorescence microscopy.

Figure 8:
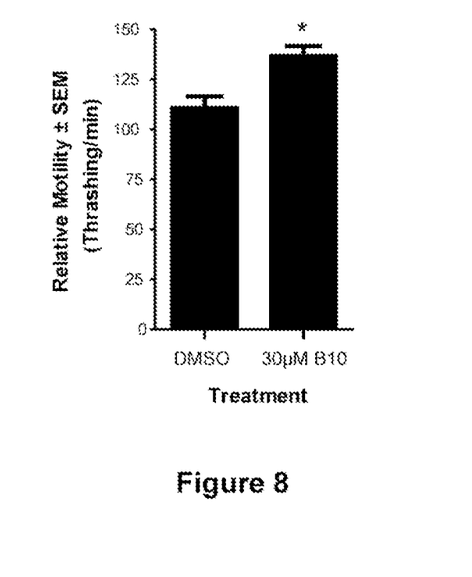
FIG. 8 is an image depicting B10 improves motility in the C25-TDP-43 transgenic *C. elegans* model.
Figure 9A:
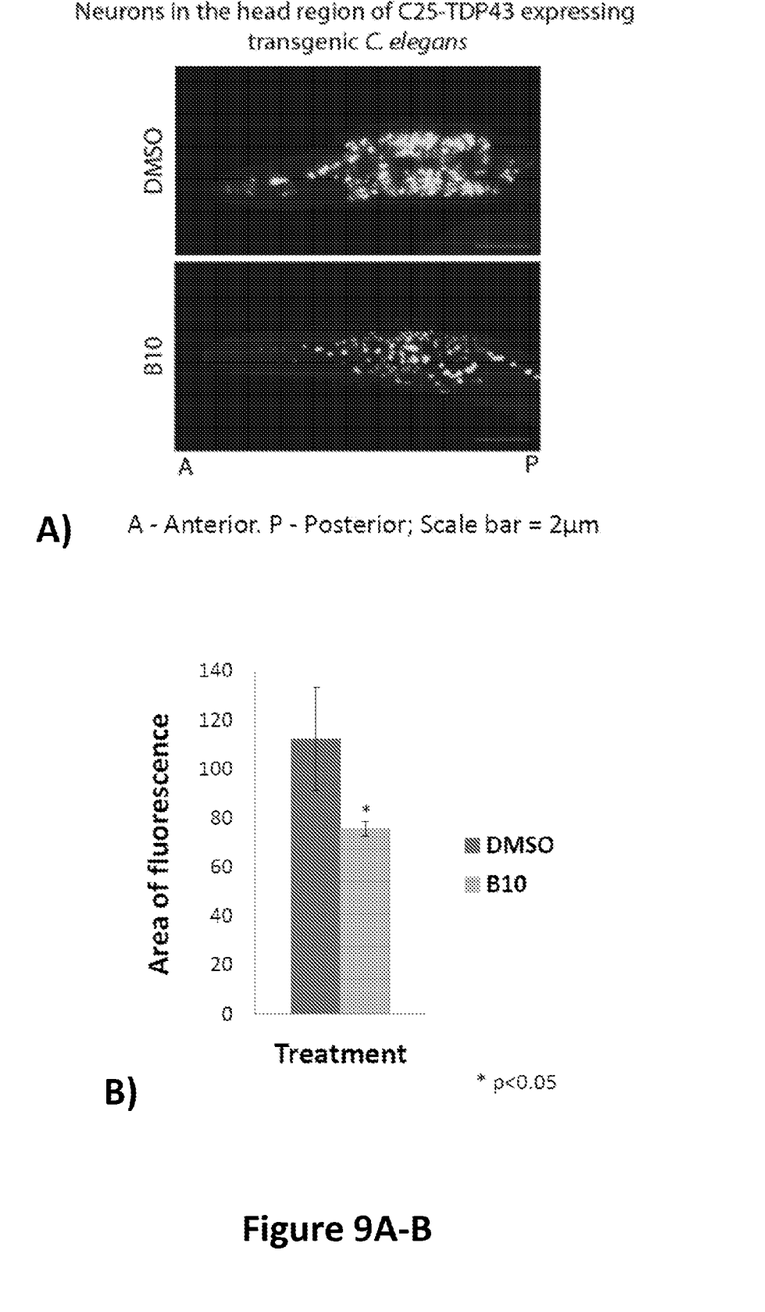

It was found that treatment with B10 improved motility of C25 worms. (FIG. 8) Additionally, treatment with B10 decreased the accumulation of TDP-43 in the neurons in the head region of C25 worms, as demonstrated by fluorescence microscopy. (FIG. 9A-B)

Prophetic Example

The inventors administer a range of dosages of hexachlorophene or one of its derivatives to a transgenic animal, such as a rat, to determine the optimal dosage as well as a range of dosages that are compatible with the organism. The hexachlorophene is administered either after pre-treatment/pre-administration with an antioxidant or other agent which has been shown to reduce the toxicity of hexachlorophene. In some embodiments, the pre-administration agent is butylated hydroxytoluene (BHT), ethoxyquin, L-carnitine, phenobarbital, or SKF-525A. The pre-administration agent is administered to the patient daily for a time period of at least one day prior to administration of the hexachlorophene.

In an alternative embodiment, no pre-administration agent is administered but the hexachlorophene is encapsulated in a vesicle such as liposomes, niosomes, micelles, multilamellar vesicles, unilamellar vesicles, and polymersomes prior to administration to the patient. Encapsulation in a vesicle ensures targeting of the drug to the correct tissues and controlled release over time.

In still another embodiment, another agent may be administered concomitantly with the hexachlorophene with this agent being capable of limiting the toxicities of hexachlorophene.

In conclusion, the inventors found that B10 potently reduces levels of TDP-43 and its mutants in multiple cell culture models. Not only is B10 effective in decreasing soluble TDP-43, but it also decreases pathological forms of TDP-43 including cytoplasmic, insoluble and high molecular weight forms of the protein. Overall, the data suggest that B10 and its derivatives are a potential drug molecule for the treatment of AD and other TDP-43 proteinopathies.

Experimental Procedures

Materials

Drugs were purchased from NIH/Evotec (US) Inc. Hexachlorophene was purchased from Sigma (Hercules, Calif.). Lipofectamine 2000, the Alexa488 goat anti-mouse IgG antibody, culture media, and Hoechst 33258 were purchased from Invitrogen (Grand Island, N.Y.). The TDP-43 antibody was purchased from Proteintech (Chicago, Ill.). The Myc tag antibody was purchased from Cell Signaling (Danvers, Mass.). Fluoromount G was purchased from Southern Biotech (Birmingham, Ala.). Odyssey blocking buffer and fluorescent secondary antibodies were purchased from LI-COR (Lincoln, Nebr.). The GAPDH antibody was purchased from Meridian Life Science (Memphis, Tenn.). Myc-tagged TDP-43 wildtype and mutant plasmids were a kind gift from Dr. Jiou Wang (Johns Hopkins University).

Cell Culture

Cell lines used in this study include N9 (mouse microglial) and HEK293. N9 cells were maintained in Opti-MEM Reduced Serum Media supplemented with 10% fetal bovine serum (FBS), penicillin/streptomycin and L-glutamine. HEK293 cells were maintained in Opti-MEM Reduced Serum Media supplemented with 10% fetal bovine serum (FBS), penicillin/streptomycin.

InCell Western (ICW)

To optimize TDP-43 targeting ICW, N9 cells were seeded in a 96-well plate and probed with different dilutions of TDP-43 antibody as previously described (Jinwal and Dickey, 2011). For the identification of candidate drug molecules, N9 cells were treated with an array of drugs for 24 hours and processed for ICW (Jinwal and Dickey, 2011). In brief, cells were fixed, washed with PBS and incubated in blocking buffer. Cells were then incubated in primary antibody to TDP-43 (1:1000) and GAPDH (1:3000) for overnight. After washing with 0.2% Tween-20 PBS, cells were incubated with fluorescently tagged secondary antibodies for 1 hour and 30 minutes. Fluorescence intensity was then recorded and quantified using the Odyssey Infrared Imaging System (LI-COR). ICW experiments were performed in duplicate.

Drug Treatment and Western Blotting

For dose response experiments, N9 cells were treated with different concentrations of B10 for 24 hours. HEK293 cells transfected with either Myc-tagged WT or mutant TDP-43 (C25, Q331K or M337V) were treated with 3 μM B10 for 24 hours. An equivalent volume of DMSO was used for control treatments for both sets of experiments. Cells were harvested as previously described (Jinwal et al., 2012). Briefly, cells were lysed in Mammalian-Protein Extraction Reagent (M-PER; Pierce, Rockford, Ill.) containing 1× protease inhibitor mixture (Calbiochem, Billerica, Mass.), 1 mM phenylmethylsulfonyl fluoride (PMSF) and 1× phosphatase inhibitor I and II cocktails (Sigma). Protein concentration was determined using the Coomassie (Bradford) Protein Assay Kit (Pierce). Samples were analyzed for Myc and GAPDH by Western blotting. Densit Drug treatment experiments were repeated at least two times.

HEK293 cells were treated with 3 and 10 μM B10 for 24 hours. An equivalent volume of DMSO was used for control treatments. Cells were harvested as previously described (Jinwal et al., 2012). Briefly, cells were lysed in Mammalian-Protein Extraction Reagent (M-PER; Pierce, Rockford, Ill.) containing 1× protease inhibitor mixture (Calbiochem, Billerica, Mass.), 1 mM phenylmethylsulfonyl fluoride (PMSF) and 1× phosphatase inhibitor I and II cocktails (Sigma). Protein concentration was determined using the Coomassie (Bradford) Protein Assay Kit (Pierce). Samples were analyzed using TDP-43, FUS, and GAPDH antibodies by Western blotting. Drug treatment experiments were performed in triplicate. For ubiquitinated protein analysis upon MG132 treatment, ubiquitin antibody (Santa Cruz Biotechnology) was used. Statistical analysis was performed using Microsoft Excel.

Biochemical Fractionation

To determine whether B10 decreases levels of both soluble and insoluble TDP-43, HEK293 cells were transfected with either Myc-tagged WT or C25 TDP-43 using Lipofectamine 2000 and treated with either DMSO or 3 μM B10 for 24 hours. Soluble and insoluble cellular fractions were collected as previously described by Liu et al. (Liu et al., 2013) with some modifications. Briefly, the cells were then washed once with cold PBS and lysed in RIPA buffer with protease and phosphatase inhibitors. Lysates were centrifuged at 55,000 rpm for 15 minutes at 4° C. and supernatants were collected as the soluble fractions. The pellets were resuspended in RIPA buffer and re-centrifuged at 55,000 rpm for 15 minutes at 4° C. to remove any contaminating proteins from the soluble fraction. The pellets were then lysed in RIPA buffer with 1% SDS, sonicated and centrifuged at 55,000 rpm for 15 minutes at 4° C. The supernatant was collected as the insoluble fraction. TDP-43 levels in the different fractions were analyzed by Western blotting. Fractionation experiments were repeated twice.

Immunofluorescence

To study clearance of the cytoplasmic C25 mutant of TDP-43 by B10, HEK293 cells were plated on coverslips and transfected with C25 TDP-43 using Lipofectamine 2000. 24 hours after transfection, the medium was replaced and cells were treated with either DMSO or 3 μM B10 for 24 hours. Cells were then washed with PBS and fixed with 3.7% formaldehyde. Following three washes in PBS, cells were incubated in blocking buffer (1% BSA, 0.1% Tween-20 in PBS) for one hour. A mouse monoclonal antibody to the Myc tag at a dilution of 1:400 was applied for 1 hour. After three washes in PBS, cells were incubated with an Alexa488 tagged goat anti-mouse IgG secondary antibody at 1:800 for 1 hour. Nuclei were stained with Hoechst 33258. Coverslips were mounted on slides using Fluoromount G. Imaging was performed with a Zeiss AxioVision imager.

Quantitation of Western Blots and Statistical Analyses

Replicate densitometric values were obtained from repeated experiments using Scion Image software. For replicate blots/experiments, standard error was calculated using Microsoft Excel.

LDH Assay.

The LDH assay was performed using the CytoTox 96 Non-Radioactive Cytotoxicity Assay from Promega as per manufacturer's instructions. Briefly, N9 and HEK cells were treated with different concentrations of hexachlorophene for 24 hours. Cells treated with a lethal dose of 150 μM hexachlorophene were used as the maximal LDH release control. Culture supernatant was collected and centrifuged at 2000 rpm to pellet debris. 50 μl of supernatant from each sample was transferred to a flat-bottom 96 well plate. The Substrate Mix provided in the kit was reconstituted with Assay Buffer. 50 μl of the reconstituted Substrate Mix was added to the culture supernatant. The plate was incubated at room temperature, protected from light, for 30 minutes. 50 μl of Stop Solution was added to each well at the end of the incubation period. Absorbance was read at 490 nm. The experiment was performed in triplicate for each cell line. Statistical analysis was performed using Microsoft Excel.

CONCLUSIONS

ICW analysis shows out of 300 drugs tested, B10 was identified as a potent TDP-43 reducing drug. B10's effect on TDP-43 was validated by treatment of microglial cells with different amounts of B10 and western blot analysis.

Wildtype and disease-associated variants of TDP-43 were tested via overexpression in HEK293 cells. Western blotting analysis showed B10 treatment caused reduction in all forms of TDP-43, including both the levels of insoluble forms of TDP-43 and of higher molecular weight species.

In in vivo studies, B10 treatment showed dramatic improvement in motility in a C25-TDP-43 expressing *C. elegans* model. It was found that B10 treatment decreases the cytoplasmic aggregates of C25-TDP-43 in the neurons in the head region of the worms.

In summary, treatment with B10 (Hexachlorophene) was found to dramatically reduce both endogenous as well as overexpressed TDP-43 levels. Overall, the data suggest B10 drug is a novel potential drug molecule for modulating levels of TDP-43 in AD and other TDP-43 proteinopathies. The previously noted toxicities of hexachlorophene can be overcome through the use of encapsulation technologies used to encapsulate the drug within a vesicle or through the administration of a pre-administration agent such as an antioxidant as disclosed herein.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described.

What is claimed is:

1. A method of treating a neurodegenerative disease characterized by accumulation of TDP-43 protein in a patient in need thereof consisting of administering a therapeutically effective amount of hexachlorophene.

2. The method of claim 1, wherein the neurodegenerative disease is selected from the group consisting of amyotrophic lateral sclerosis (ALS), Alzheimer's disease (AD) and fronto-temporal lobar dementia (FTLD).

3. The method of claim 1, further comprising encapsulating the hexachlorophene in a vesicle prior to administration to the patient.

4. The method of claim 3, wherein the vesicle is selected from the group consisting of liposomes, niosomes, micelles, multilamellar vesicles, unilamellar vesicles, and polymersomes.

5. A method of decreasing TDP-43 accumulation in cells comprising contacting the cells with a therapeutically effective amount of hexachlorophene.

6. The method of claim 5, further comprising contacting the cells with a pre-administration agent at a time period prior to administration of the hexachlorophene wherein the pre-administration agent is selected from the group consisting of butylated hydroxytoluene (BHT), ethoxyquin, or SKF-525A.

7. The method of claim 5, further comprising encapsulating the hexachlorophene in a vesicle prior to contacting the cells.

8. The method of claim 7, wherein the vesicle is selected from the group consisting of liposomes, niosomes, micelles, multilamellar vesicles, unilamellar vesicles, and polymersomes.

9. A method of inhibiting formation of TDP-43 aggregates in cells comprising contacting the cells with a therapeutically effective amount of hexachlorophene.

10. The method of claim 9, further comprising contacting the cells with a pre-administration agent at a time period prior to administration of the hexachlorophene wherein the pre-administration agent is selected from the group consisting of butylated hydroxytoluene (BHT), ethoxyquin, or SKF-525A.

11. The method of claim 9, further comprising encapsulating the hexachlorophene in a vesicle prior to contacting the cells.

12. The method of claim 11, wherein the vescicle is selected from the group consisting of liposomes, niosomes, micelles, multilamellar vesicles, unilamellar vescicles, and polymersomes.

* * * * *